(12) United States Patent
Kern et al.

(10) Patent No.: US 10,987,134 B2
(45) Date of Patent: *Apr. 27, 2021

(54) INTRODUCTION AND ANCHORING TOOL FOR AN IMPLANTABLE MEDICAL DEVICE ELEMENT

(71) Applicant: Medtronic, Inc., Minneapolis, MN (US)

(72) Inventors: Michael J. Kern, St. Louis Park, MN (US); Bruce A. Behymer, Grant, MN (US); Bruce R. Mehdizadeh, Boise, ID (US)

(73) Assignee: Medtronic, Inc., Minneapolis, MN (US)

(*) Notice: Subject to any disclaimer, the term of this patent is extended or adjusted under 35 U.S.C. 154(b) by 314 days.

This patent is subject to a terminal disclaimer.

(21) Appl. No.: 16/224,315

(22) Filed: Dec. 18, 2018

(65) Prior Publication Data
US 2019/0125403 A1 May 2, 2019

Related U.S. Application Data

(63) Continuation of application No. 14/357,325, filed as application No. PCT/US2012/063026 on Nov. 1, 2012, now Pat. No. 10,206,710.

(Continued)

(51) Int. Cl.
*A61B 17/34* (2006.01)
*A61N 1/05* (2006.01)

(52) U.S. Cl.
CPC ...... *A61B 17/3468* (2013.01); *A61B 17/3415* (2013.01); *A61N 1/05* (2013.01)

(58) Field of Classification Search
CPC ...... A61N 1/05; A61N 1/0551; A61N 1/0558; A61N 1/057; A61N 1/056; A61N 1/0587; A61N 1/02; A61N 1/0509; A61N 1/0053; A61N 1/0573; A61N 1/0575; A61N 1/36007; A61N 2001/0582; A61N 2001/0578; A61M 25/02; A61M 25/04;
(Continued)

(56) References Cited

U.S. PATENT DOCUMENTS

| 4,437,475 A | 3/1984 | White |
| 4,624,266 A | 11/1986 | Kane |

(Continued)

FOREIGN PATENT DOCUMENTS

WO 2010/117810 A1 10/2010

OTHER PUBLICATIONS

International Preliminary Report on Patentability from International Application No. PCT/US2012/063026, dated May 13, 2014, 10 pp.
(Continued)

*Primary Examiner* — Mohamed G Gabr
(74) *Attorney, Agent, or Firm* — Shumaker & Sieffert, MN

(57) ABSTRACT

In some examples, an apparatus may include a needle configured to define a path through tissue of a patient, tubing configured to slidably receive the needle via a proximal opening, an anchor configured to slidably receive at least a portion of the tubing, and an anchor deployment member comprising a body and an anchor engagement member. Such an apparatus may be used to introduce and anchor an implantable medical device within a patient.

25 Claims, 11 Drawing Sheets

Related U.S. Application Data

(60) Provisional application No. 61/558,295, filed on Nov. 10, 2011.

(58) Field of Classification Search
CPC .......... A61M 25/0612; A61M 25/0662; A61M 2025/028; A61M 2025/0213; A61M 2025/0286; A61M 2025/0293; A61B 17/0401; A61B 17/0469; A61B 17/0487; A61B 17/3421; A61B 18/1477; A61B 2017/0039; A61B 2017/00238; A61B 2017/0409; A61B 2017/0445; A61B 2017/0464; A61B 2017/061; A61B 2017/22038; A61B 2018/00273; A61B 2090/062
USPC .................. 606/129, 151, 153; 604/175–179
See application file for complete search history.

(56) References Cited

U.S. PATENT DOCUMENTS

| | | |
|---|---|---|
| 5,284,141 A | 2/1994 | Eibling |
| 5,397,342 A | 3/1995 | Heil et al. |
| 5,746,722 A | 5/1998 | Pohndorf et al. |
| 5,824,032 A | 10/1998 | Belden |
| 5,827,296 A | 10/1998 | Morris et al. |
| 7,748,124 B1 | 7/2010 | Bell et al. |
| 10,206,710 B2 | 2/2019 | Kern et al. |
| 2002/0147485 A1 | 10/2002 | Mamo et al. |
| 2003/0135253 A1 | 7/2003 | Kokones et al. |
| 2005/0080470 A1 | 4/2005 | Westlund et al. |
| 2006/0122676 A1 | 6/2006 | Ko et al. |
| 2007/0100411 A1 | 5/2007 | Bonde |
| 2007/0173900 A1 | 7/2007 | Siegel |
| 2008/0103573 A1 | 5/2008 | Gerber |
| 2008/0275401 A1 | 11/2008 | Sage et al. |
| 2009/0198197 A1 | 8/2009 | Bischoff et al. |
| 2009/0248054 A1* | 10/2009 | Sage ................. A61M 25/04 606/174 |
| 2010/0094341 A1 | 4/2010 | Raju |
| 2010/0185161 A1 | 7/2010 | Pellegrino et al. |
| 2010/0312256 A1 | 12/2010 | Kassab et al. |
| 2011/0040257 A1 | 2/2011 | Behymer et al. |

OTHER PUBLICATIONS

Preliminary Amendments in counterpart European Application No. 12788690.1, filed on May 23, 2014, 4 pp.
Response to Communication under Rule 161(1) EPC from counterpart European Application No. 12788690.1, filed on Mar. 26, 2015, 4 pp.
Intention to Grant from counterpart European Application No. 12788690.1, dated Oct. 9, 2017, 39 pp.
International Search Report and Written Opinion of International Application No. PCT/US2012/063026, dated Feb. 8, 2013, 15 pp.
Prosecution History from U.S. Appl. No. 14/357,325, dated Nov. 10, 2016 through Dec. 26, 2018,142 pp.

* cited by examiner

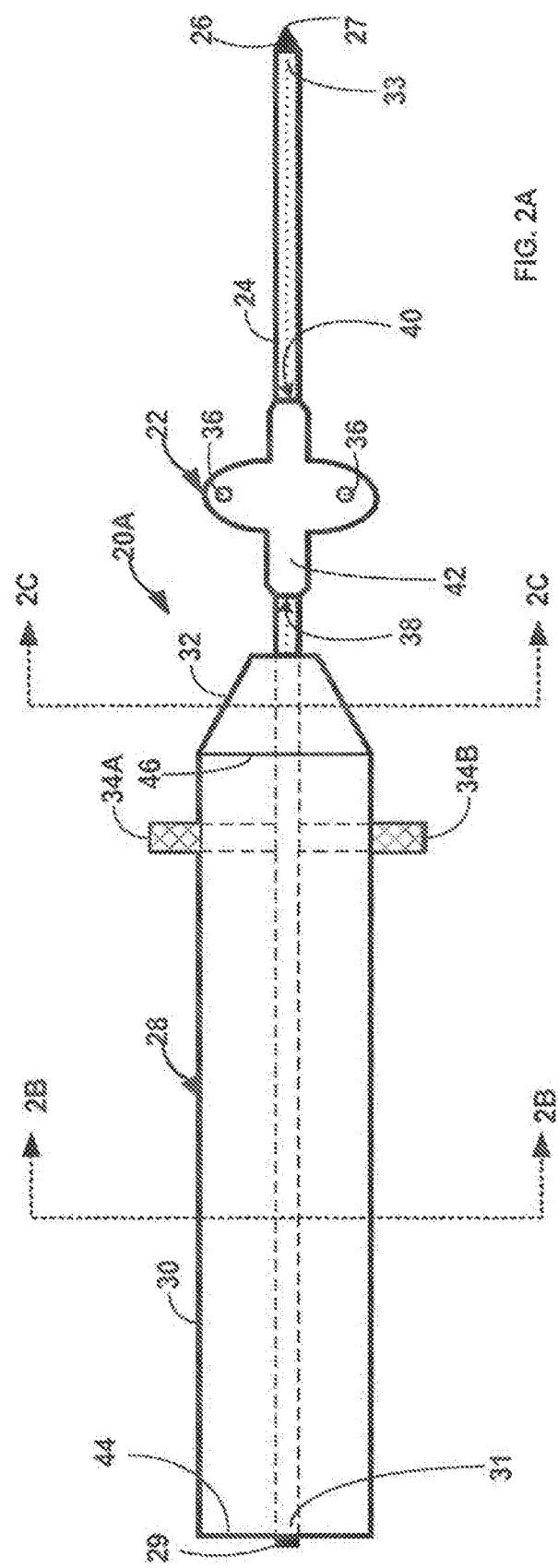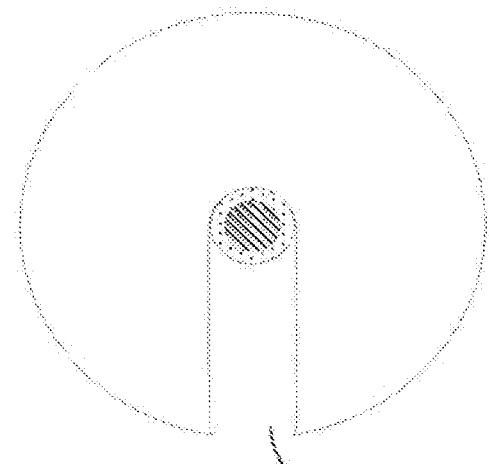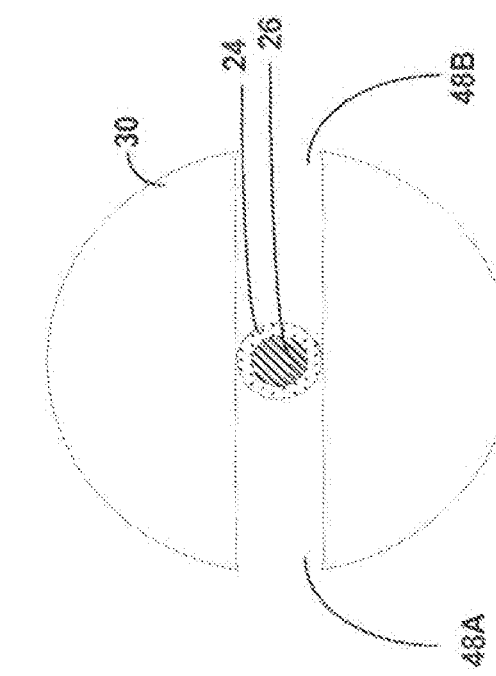

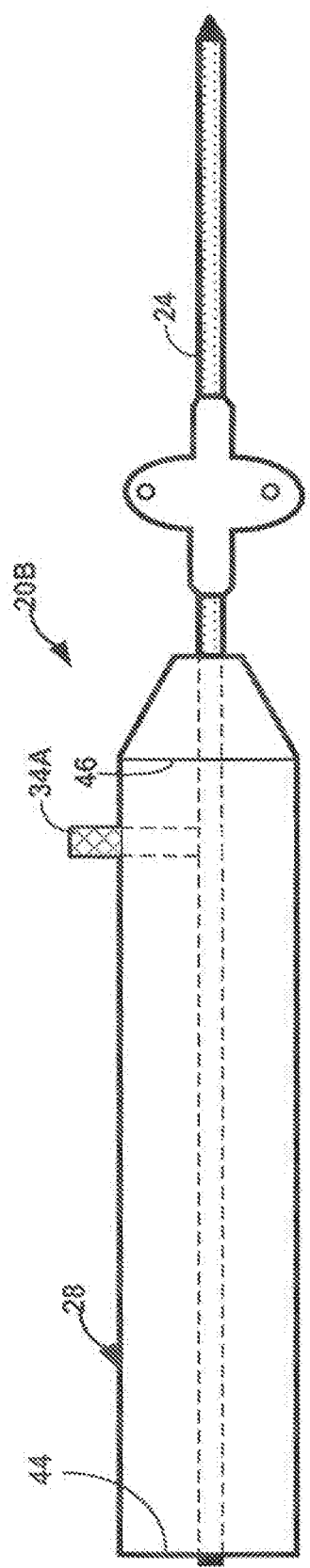

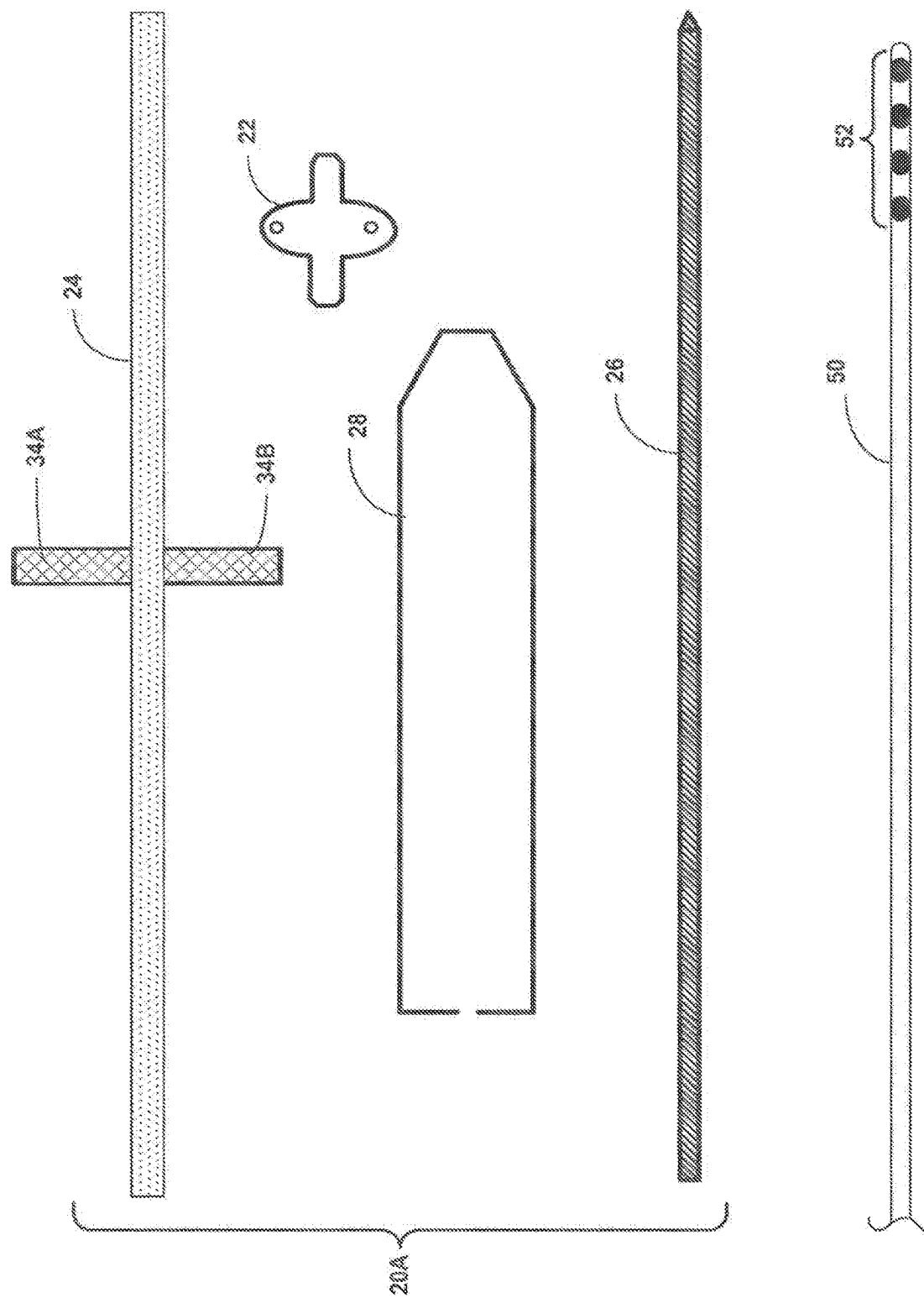

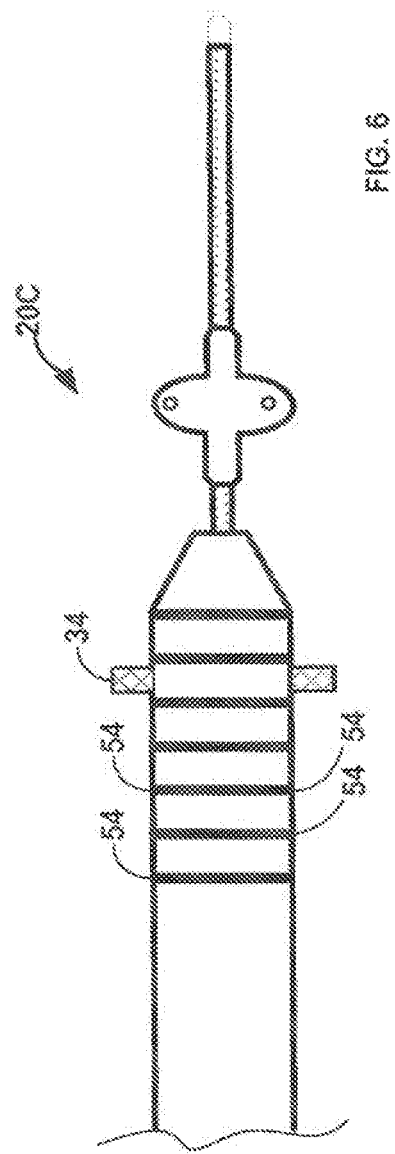

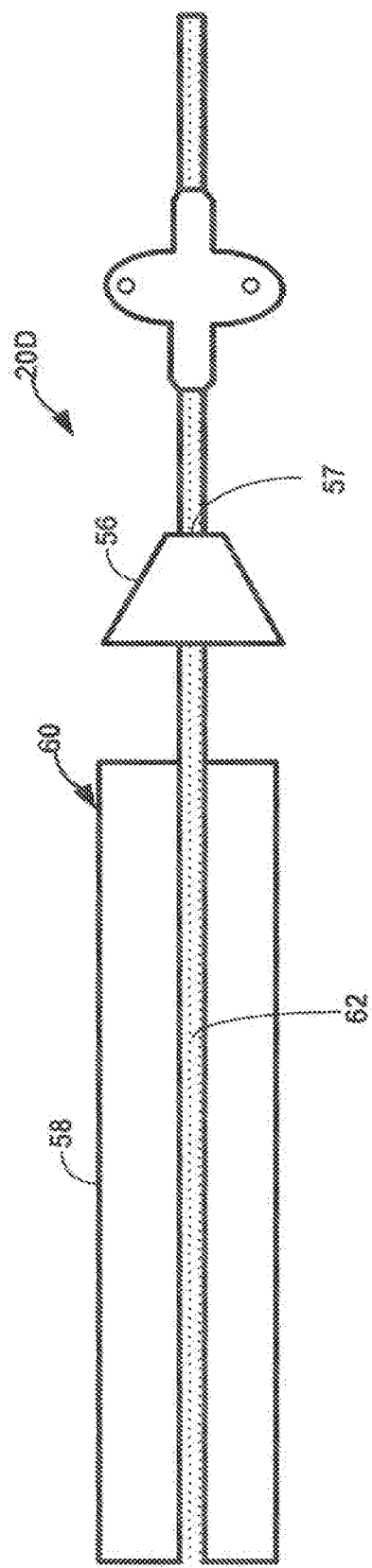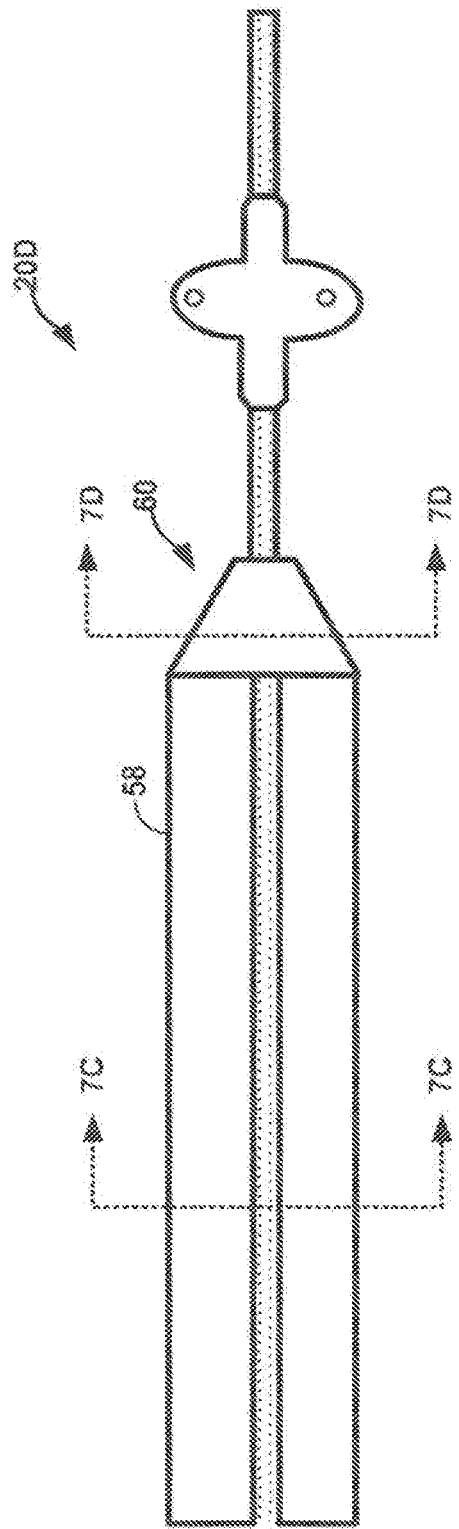

INTRODUCTION AND ANCHORING TOOL FOR AN IMPLANTABLE MEDICAL DEVICE ELEMENT

PRIORITY CLAIM

This application is a continuation of U.S. patent application Ser. No. 14/357,325, filed on May 9, 2014, which is National Stage Entry of International Patent Application No. PCT/US2012/063026, filed on Nov. 1, 2012, which claims the benefit and priority under 35 U.S.C. § 119(e) from U.S. Provisional Patent Application No. 61/558,295, filed on Nov. 10, 2011. Application Ser. No. 14/357,325, PCT/US2012/063026, and 61/558,295 are hereby incorporated by reference in their entirety.

TECHNICAL FIELD

The disclosure relates to systems and techniques for introducing and anchoring implantable medical device elements.

BACKGROUND

Implantable medical device (IMD) elements, such as medical leads and catheters, have been employed for a variety of therapeutic and diagnostic purposes. Controlled placement of such IMD elements within a patient is highly desirable, as precise placement may result in, for example, more reliable sensing, improved therapeutic efficacy or reduced side effects.

In some examples, the location of the IMD element may change over time. For example, patient movement may cause movement of the IMD element. Thus, in some cases, a fixation or anchoring mechanism may be employed to limit movement of the IMD element within the patient.

SUMMARY

In general, the disclosure is directed to a tool configured for introducing and anchoring an IMD element in tissue of a patient. The tool may be used to deploy an IMD element such as a catheter or electrical lead within patient tissue.

In one example, the disclosure is directed to an apparatus comprising a first elongated member defining a proximal end and a distal end, the first elongated member configured to define a path through tissue of a patient for insertion of an implantable medical device into the path, a second elongated member defining a proximal opening, a distal opening, and a lumen extending between the proximal opening and the distal opening, the lumen configured to slidably receive at least a portion of the first elongated member and at least a portion of the implantable medical device via the proximal opening, an anchor defining an anchor lumen configured to slidably receive at least a portion of the second elongated member, and an anchor deployment member. The anchor deployment member comprises a body defining a channel through which the first elongated member, the second elongated member, and the implantable medical device are slidable, and an anchor engagement member configured to bear against the anchor when the second elongated member is moved in a proximal direction relative to the body such that the second elongated member is withdrawn from the anchor lumen.

In another example, the disclosure is directed to a method comprising defining a path through tissue of a patient for insertion of an implantable medical device into the path, wherein defining the path through tissue of the patient comprises tunneling through tissue of the patient with a first elongated member of a medical device apparatus. The medical device apparatus comprises the first elongated member defining a proximal end and a distal end, a second elongated member defining a proximal opening, a distal opening, and a lumen extending between the proximal opening and the distal opening, the lumen configured to slidably receive at least a portion of the first elongated member and at least a portion of the implantable medical device via the proximal opening, an anchor defining an anchor lumen configured to slidably receive at least a portion of the second elongated member, and an anchor deployment member. The anchor deployment member comprises a body defining a channel through which the first elongated member, the second elongated member, and the implantable medical device are slidable, and an anchor engagement member configured to bear against the anchor when the second elongated member is moved in a proximal direction relative to the body such that the second elongated member is withdrawn from the anchor lumen.

The details of one or more examples are set forth in the accompanying drawings and the description below. Other features, objects, and advantages of the disclosure will be apparent from the description and drawings, and from the claims.

BRIEF DESCRIPTION OF DRAWINGS

FIGS. 2A-2C are schematic diagrams of an example tool configured for introducing and anchoring an IMD element in a patient.

FIG. 3 is a schematic diagram of another example tool configured for introducing and anchoring an IMD element in a patient.

FIG. 4A is a schematic diagram illustrating an exploded view of the tool of FIGS. 2A-2C, along with an IMD element that may be introduced and implanted using the tool.

FIG. 6 is a schematic diagram illustrating an example tool that includes distance markings on an outer surface of the tool.

FIGS. 7A-7D are schematic diagrams illustrating an example tool that includes an anchor deployment member including a separable end portion.

DETAILED DESCRIPTION

As mentioned above, the disclosure is directed to a tool and techniques for using a tool that includes components configured for introducing and anchoring an IMD element in tissue of a patient. As described in further detail below, the tool may include a first elongated member, such as a needle, configured to define a path through tissue of the patient and a second elongated member defining a lumen that is configured to receive at least a portion of the first elongated member. The mechanical properties of the second elongated member may allow the second elongated member to maintain the defined path within the tissue such that an IMD element can be inserted into the path. The tool also includes an anchor defining a lumen; the anchor may be configured to fix the IMD element within the tissue of the patient to prevent or minimize movement of the IMD element within the tissue. The second elongated member and, subsequently, the IMD element, may be at least partially positioned within the lumen of the anchor. The tool further includes an anchor deployment member configured to deploy the anchor around the IMD element upon implantation of the IMD element.

A tool that includes components configured for both introducing and anchoring an IMD element in tissue of a patient may provide one or more advantages. For example, a single tool that includes both introducing and anchoring components may reduce the amount of tools or devices required for implanting an IMD element in tissue of a patient and, consequently, may reduce the amount of tools exchanged during an implantation procedure. Reducing the amount of tools required and exchanged during implantation may reduce the complexity of the implantation procedure, thus reducing the time spent in the operating room for both the patient and a physician and increasing the ease of use for the physician.

In some examples, the apparatuses described herein may be useful for implanting an IMD element, such as an electrical stimulation lead or a catheter within subcutaneous tissue of a patient. For example, the apparatuses described herein may be useful in implanting an IMD element proximate to any of a variety of peripheral nerves of the patient, e.g., in the back, abdomen, pelvic floor, neck, limbs, or elsewhere in the patient. As one illustration, the apparatus described in this disclosure may be used to implant an IMD element proximate to an occipital nerve, as described in further detail below.

Figure 1:
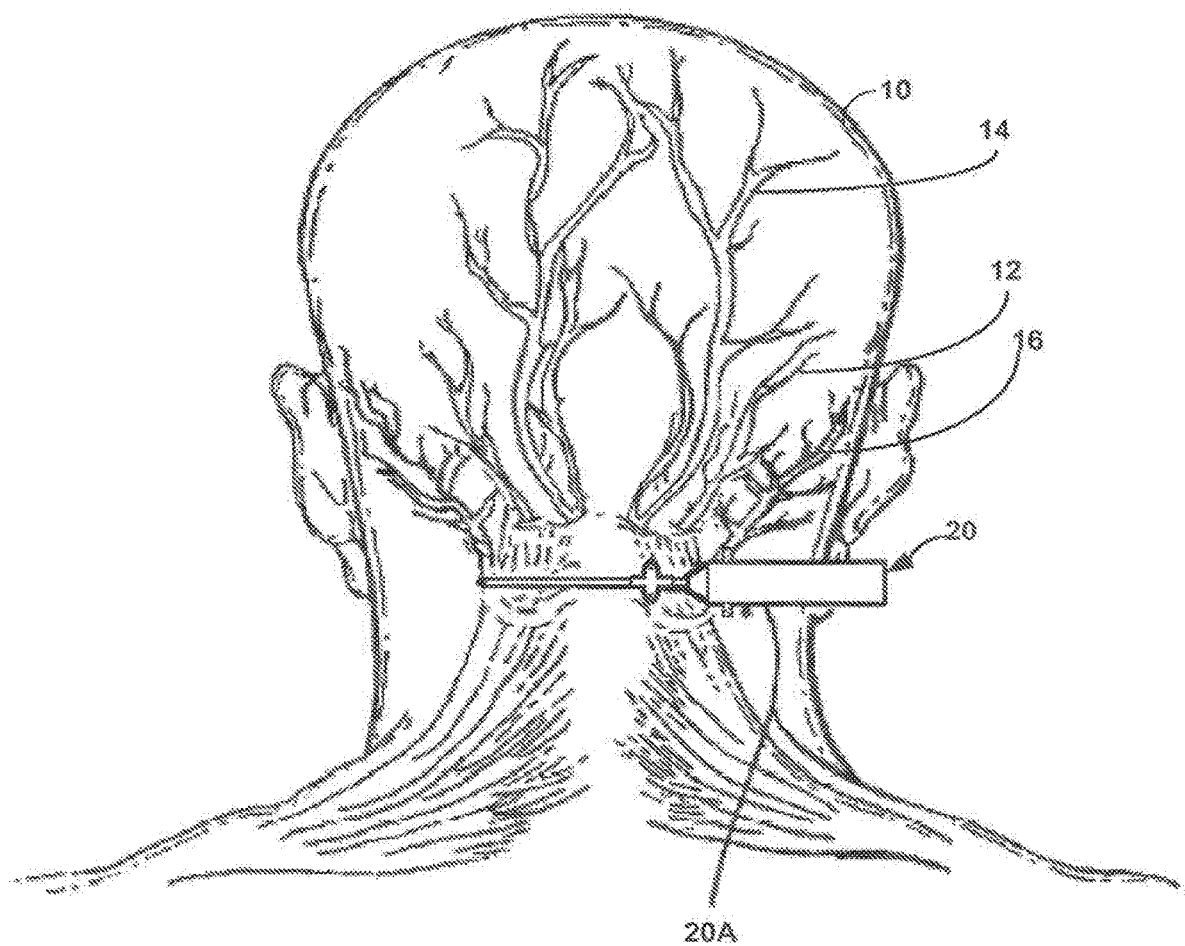
FIG. 1 is a schematic diagram of a patient and a tool configured to introduce and anchor an IMD element subcutaneously in the patient.

FIG. 1 is a schematic view of a head and torso of patient 10, in which a lesser occipital nerve 12, greater occipital nerve 14, and third occipital nerve 16 of patient 10 are shown. Occipital nerves 12, 14, and 16 generally extend upward from a spinal cord of patient 10 to the back and sides of the head.

FIG. 1 illustrates an exemplary apparatus 20 configured for introducing and anchoring an IMD element. In the example illustrated in FIG. 1, apparatus 20 facilitates introduction and anchoring of an IMD element in subcutaneous tissue of patient 10 proximate to one of the occipital nerves 12, 14, and 16 of patient 10. In other examples, the IMD element may be introduced and anchored, via apparatus 20, proximate to one or more other peripheral nerves of patient 10, such as nerves branching from occipital nerves 12, 14, or 16.

In some examples, delivery of therapy, e.g., electrical stimulation therapy or drug therapy, to a target tissue site proximate to occipital nerves 12, 14, and/or 16 may help alleviate pain associated with, for example, chronic migraines, cervicogenic headaches, occipital neuralgia or trigeminal neuralgia.

Although FIG. 1 illustrates the use of apparatus 20 to implant an IMD element proximate to occipital nerves 12, 14, and/or 16, in other examples, the IMD element may be positioned proximate to another suitable nerve, organ, muscle, or muscle group within patient 10, which may be selected based on, for example, a particular therapy program selected for patient 10. For example, the IMD element may be used to deliver therapy to a sacral nerve, a pudendal nerve, a perineal nerve, a trigeminal nerve or other areas of the nervous system, in which cases, the IMD element would be implanted and substantially fixed proximate to the respective nerve.

As further examples, the IMD element may be positioned for temporary or chronic spinal cord stimulation for the treatment of pain, for peripheral neuropathy or post-operative pain mitigation, ilioinguinal nerve stimulation, intercostal nerve stimulation, gastric stimulation for the treatment of gastric mobility disorders and obesity, muscle stimulation (e.g., functional electrical stimulation (FES) of muscles), for mitigation of other peripheral and localized pain (e.g., leg pain or back pain), or for deep brain stimulation to treat movement disorders and other neurological disorders.

In some examples, the IMD element is configured to couple to a therapy delivery source, such as an electrical stimulation generator or a fluid delivery device. For example, the IMD element may be a stimulation lead or a lead extension that is used to deliver electrical stimulation to a target stimulation site and/or sense parameters (e.g., blood pressure, temperature or electrical activity) proximate to a target site within a patient. In another example, the IMD element may be a catheter that is placed to deliver a fluid, such as pharmaceutical agents, insulin, pain relieving agents, gene therapy agents or the like from a fluid delivery device (e.g., a fluid reservoir and/or pump) to the target tissue site within the patient. In yet another example, the IMD element may be a microstimulator that may be implanted within tissue of a patient to deliver stimulation to the tissue. Thus, in some embodiments, "therapy" may include stimulation therapy, sensing or monitoring of one or more physiological parameters, fluid delivery, and the like. "Target tissue site" refers generally to the target site for implantation of an elongated member, regardless of the type of therapy.

In some examples of implanting an IMD element proximate to one or more occipital nerves 12, 14, 16, a vertical skin incision approximately two centimeters in length is made in the neck of patient 10 lateral to the midline of the spine at the level of the C1 vertebra. Fluoroscopy may be used to identify the location of the C1 vertebra. Typically, local anesthetic is used during the implantation procedure. The length of vertical skin incision may vary depending on the particular patient. At this location, the patient's skin and muscle are separated by a band of connective tissue referred to as fascia. In another technique, an incision is made in trapezius muscle of patient 10. Subsequently, tool 20 may be utilized to introduce an IMD element into the incision. In some examples, once the distal end of the IMD element is positioned and anchored at the target tissue site within patient 10, the proximal end of the IMD element may be tunneled within tissue of patient 10 to, for example, an electrical stimulation generator or a fluid delivery pump in a subcutaneous pocket remote from the target tissue site.

FIG. 2A is a schematic diagram illustrating tool 20A configured for introducing and anchoring an IMD element within tissue of a patient. As illustrated in FIG. 2A, tool 20A includes anchor 22, tubing 24, needle 26 (defining distal tip 27 and proximal end 29), anchor deployment member 28, and actuators 34A and 34B (collectively referred to as "actuators 34"). Anchor deployment member 28 includes body 30 and anchor engagement member 32. As illustrated in FIG. 2A and described in further detail below, tool 20A includes two actuators 34. FIG. 3, described below, illustrates exemplary tool 20B including only one actuator 34.

A clinician or other user may use tool 20A to introduce and anchor an IMD element (e.g., a catheter or a medical lead) at a target tissue site within patient 10. For example, the clinician or other user may insert distal tip 27 of needle 26 into tubing 24 via proximal end 31 of tubing 24. As illustrated in FIG. 2A, distal tip 27 may exit tubing 24 via distal end 33 of tubing 24. The clinician or other user may subsequently insert tubing 24 at least partially containing needle 26 into tissue of patient 10 and tunnel tubing 24 and needle 26 through the tissue to a target tissue site. After tubing 24 and needle 26, e.g., distal tip 26A of needle 26, reach the target tissue site, the clinician or other user may extract needle 26 from within tubing 24 such that tubing 24 remains within the path defined by tubing 24 and needle 26. Subsequently, the clinician or other user may insert an elongated IMD element into tubing 24 to position the IMD element at the target tissue site. After positioning the IMD element at a desired position relative to the target tissue site, the clinician or other user may deploy anchor 22 around the IMD element to secure the IMD element at the target tissue site. In some examples, the clinician may suture the anchor 22 to tissue of the patient to secure the anchor 22 in place.

As described in further detail below, anchor 22 is formed from an at least partially elastic material such that anchor 22 contracts around tubing 24. As illustrated by hidden lines in FIG. 2A, actuators 34 are coupled to tubing 24 within anchor deployment member 28. In order to deploy anchor 22 onto the IMD element, the clinician or other user may apply a force to actuators 34 to pull actuators 34 proximally such that tubing 24 moves proximally within anchor deployment member 28. Anchor 22, which is contracted around tubing 24, may also move proximally as tubing 24 moves proximally until anchor 22 abuts anchor engagement member 32. The clinician or other user may continue to pull actuators 34 proximally such that tubing 24 is retracted into anchor deployment member 28 from within anchor 22, anchor engagement member 32 pushes against anchor 22, and anchor 22 is deployed onto the IMD element. In particular, as tubing 24 is withdrawn from the inner lumen of anchor 22, the outer surface of the IMD element is exposed such that anchor 22 contacts the IMD element. For example, the outer diameter of the tubing 24 pushing on the inner diameter of the anchor lumen may cause the elastic anchor 22 to expand outward such that, when tubing 24 is retracted or withdrawn into anchor deployment member 28 from within anchor 22, anchor 22 elastically contracts on the IMD element. In some examples, the clinician or another user may suture the anchor 22 to tissue of the patient to anchor the anchor 22 within the tissue, e.g., via suture holes 36 of anchor 22.

In the example illustrated in FIG. 2A, anchor 22 defines a proximal opening 38, a distal opening 40, and body 42 extending between the proximal opening 38 and distal opening 40. A lumen (not shown) extends through body 42 between proximal opening 38 and distal opening 40, and is configured to receive, for example, tubing 24 or an elongated portion of an IMD element.

At least a portion of body 42 is radially stretchable such that the body 42 has a first inner diameter (defined by the lumen extending through anchor 22) in a relaxed state and a second larger inner diameter in a stretched state, e.g., when anchor 22 is deployed around tubing 24. Body 42 of anchor 22 may be formed from any suitable elastic material. For example, body 42 may be formed from copolymers of styrene-butadiene, polybutadiene, polymers formed from ethylene-propylene diene monomers, polychloroprene, polyisoprene, copolymers of acrylonitrile and butadiene, copolymers of isobutyldiene and isoprene, polyurethanes and the like. In some examples, body 42 may be formed of material capable of being stretched up to about 50% or more without substantial loss of structural integrity. In some examples, body 42 may be made from the same material as the remaining portions of anchor 22 while, in other examples, body 42 and the remaining portions of anchor 22 may be made from different materials.

Body 42 of anchor 22 defines an anchor lumen that is configured to slidably receive the tubing 24. That is, a clinician or other user may slide tubing 24 into the anchor lumen defined within body 42 of anchor 22. Anchor 22 may have any configuration suitable for being deployed around an IMD element using tool 20A to secure the IMD element proximate to a target tissue site. For example, several additional exemplary configurations for anchor 22 are illustrated in FIGS. 8A-8D, and described in further detail below. In addition, U.S. Patent Application Publication No. 2011/0040257, published Feb. 17, 2011, to Behymer et al., entitled "ANCHOR DEPLOYMENT APPARATUS," describes various anchor configurations.

Tubing 24 defines a proximal opening in proximal end 31, a distal opening in distal end 33, and a lumen extending between the proximal opening and the distal opening. As described herein, the lumen extending between the proximal opening and the distal opening is configured to slidably receive the needle 26 and an IMD element, such as a medical lead or catheter. For example, a clinician or other user may slide needle 26 and/or an elongated IMD element (e.g., IMD element 50 illustrated in FIG. 4) into the lumen of tubing 24 via the proximal opening.

Tubing 24 may have any configuration suitable for receiving (in some examples, at different times) needle 26 and an IMD element implanted within tissue of patient 10, and for maintaining a path within the tissue of the patient into which the IMD element may be inserted. For example, tubing 24 may be formed from a metal or metal alloy such as stainless steel, nitinol, titanium, or tungsten. In other examples, tubing 24 may be formed from a polymer such as polyether ether ketone (PEEK) or polyethylene terephthalate (PET).

Tubing 24 extends between proximal end 29 and distal end 33. In the example illustrated in FIG. 2A, tubing 24 forms a substantially straight tube with a circular cross-section (as illustrated in FIGS. 3A and 3B). In other examples, tubing 24 may have another configuration. For example, in some examples, tubing 24 may have a substantially curvilinear configuration instead of a straight configuration.

In some examples, the configuration of tubing 24 may be selected to facilitate tunneling of tubing 24 within a particular portion of the body of patient 10. e.g., around particular organs or internal body parts of patient 10. For example, tubing 24 may be formed to be flexible such that tubing 24 can easily tunnel through and adapt to the contour of tissue of patient 10. For example, tubing 24 may include etchings or laser cut regions along the length of tubing 24 between proximal end 27 and distal end 33 that allow portions of tubing 24 to bend. As an example, tubing 24 may include several etchings or laser cut regions extending around the circumference of tubing 24 that allow tubing 24 to be bendable in various directions. In some examples, the clinician or another user implanting IMD element 50 may bend the tubing 24 during insertion. In some examples, flexible tubing 24 may allow the tubing 24 to be easily bendable while maintaining a sufficient shape upon deployment of anchor 22, e.g., when tubing 24 passes through anchor 22 to deploy anchor 22 onto an IMD element.

Needle 26 defines a proximal end 29 and a distal end 27, and is configured to define a path through tissue of patient 10 for insertion of an IMD element into the path. In some examples, distal end 27 of needle 26 is specifically configured to tunnel through tissue of patient 10. For example, in the example illustrated in FIG. 2A, distal end 27 of needle 26 forms a sharp point configured to push through tissue of patient 10, thereby defining a path through the tissue.

In some examples, needle 26 may also define a lumen configured to receive an IMD element, such as a medical lead or a catheter. In this way, a clinician or other user may introduce needle 26 into tubing 24, tunnel needle 26 and tubing 24 to a target tissue site within patient 10, and subsequently introduce the IMD element into the lumen defined within needle 26 prior to withdrawing needle 26 from tubing 24. In other examples, needle 26 may not be configured to accept the IMD element and, consequently, the clinician or other user may withdraw needle 26 from tubing 24 and, subsequently, slidably introduce the IMD element into tubing 24 proximate to the target tissue site.

As illustrated in FIG. 2A, needle 26 is positioned within tubing 24 such that needle 26 and tubing 24 can collectively tunnel through tissue of patient 10 to define a path for an IMD element. As mentioned above, in some examples, a clinician or other user may insert needle 26 into tubing 24 via the proximal opening defined by tubing 24. In the example illustrated in FIG. 2A, the proximal end 29 of needle 26 extends outward from tubing 24 and anchor deployment member 28, and is visible at the proximal end of the assembly. In other examples, needle 26 may be flush with the side of the anchor deployment member 28 and may not extend past the side. In yet other examples, needle 26 may include a handle mechanism attached to proximal end 29 of needle 26 that facilitates easy manipulation of needle 26 by a user.

In some examples, needle 26 may be manually curved by the clinician or other user to conform to the contour of the body of patient 10 proximate to the target tissue site, such as the contour of the neck of patient 10 in the example illustrated in FIG. 1. In other embodiments, introducer needle 32 may have a preformed curve or other configuration. Needle 26 may be formed from any material suitable for defining a path through tissue of the patient 10. For example, needle 26 may be formed from a metal or metal alloy such as stainless steel, nitinol, titanium, or tungsten. In other examples, needle 26 may be formed from a polymer such as polyether ether ketone (PEEK).

Anchor deployment member 28 comprises body 30, extending between proximal end 44 and distal end 46, and distal anchor engagement member 32. Body 30 of anchor deployment member 28 defines a channel through which the needle 26, the tubing 24, and an IMD element (e.g., a medical lead or catheter) are slidable. That is, body 30 defines a channel configured to slidably receive needle 26, tubing 24, and an IMD element. Distal anchor engagement member 32 is configured to bear against anchor 22 when tubing 24 is moved in a proximal direction relative to body 30 such that tubing 24 is withdrawn from the anchor lumen of anchor 22.

In the example illustrated in FIG. 2A, tubing 24 extends through anchor deployment member 28 and actuators 34 are coupled to tubing 24 within anchor deployment member 28 such that movement of actuators 34 in a proximal or distal direction results in movement of tubing 24 in a proximal or distal direction, respectively. If needle 26 or an IMD element is positioned within tubing 24, the movement of tubing 24 in the proximal or distal direction may be relative to needle 26 or the IMD element positioned within tubing 24, e.g., needle 26 or the IMD element may remain substantially stationary while tubing 24 moves in the proximal or distal direction. In this way, a clinician or other user may apply a force to actuators 34 to pull or push actuators 34 in a proximal or distal direction in order to move tubing 24 in a proximal or distal direction with respect to needle 26 or an IMD element positioned within tubing 24, e.g., to deploy anchor 22 around an IMD element.

As illustrated in FIG. 2A, actuators 34 may be coupled to tubing 24 within body 30 of anchor deployment member 28 and extend out of body 30 through the pathways or grooves defined within body 30, as described above. Actuators 34 may be coupled to tubing 24 in any suitable manner. For example, in some examples, actuators 34 may be adhered to an outer surface of tubing 24 via an adhesive. In other examples, actuators 34 and tubing 24 may be integrally formed, e.g., molded, as a collective unit.

FIG. 2B illustrates a cross-section of anchor deployment member 28 of tool 20A taken along the line 2B-2B shown in FIG. 2A. As illustrated in FIG. 2B, body 30 of anchor deployment member 28 may define grooves 48A and 48B (collectively referred to as "grooves 48") such that actuators 34A and 34B, respectively, can move proximally and distally within anchor deployment member 28. For example, body 30 may be formed, e.g., molded, to define two grooves 48A and 48B, each of which is configured to receive one of actuators 34, extending between proximal end 44 and distal end 46 of body 30. In some examples, the pathways or grooves 48 may only extend over a portion of body 30 between proximal end 44 and distal end 46 such that actuators 34 may only be slidable over a portion of body 30 because the pathways or grooves 48 may constrain movement of actuators 34 to within only a portion of body 30. In other examples, the pathways or grooves 48 may extend substantially entirely between proximal end 44 and distal end 46 such that the actuators 34 may have a full range of motion over body 30. The amount of movement of actuators 34 allowed by the pathways or grooves may directly correlate to the amount of movement allowed for tubing 24.

FIG. 2C illustrates a cross-section of anchor deployment member 28 of tool 20A taken along line 2C-2C shown in FIG. 2A. In the example illustrated in FIG. 2C, groove 48A is defined within anchor deployment member 28 extending between body 30 (e.g., as illustrated by the cross-section shown in FIG. 2B) substantially completely through anchor engagement member 32 of anchor deployment member 28. In some examples, a configuration that includes one or more grooves 48 extending through both body 30 and anchor engagement element 32 of anchor deployment member 28 may reduce the complexity of placing tubing 24 within the lumen defined by anchor deployment member 28. For example, the tubing 24 may be positioned within anchor deployment member 28 through the groove 48A when tool 20A is assembled, e.g., in a substantially sideways fashion. In some examples, positioning of tubing 24 within anchor deployment member 28 via groove 48 may be less complex for a user than inserting tubing 24 into the proximal end of anchor deployment member 28, during assembly of tool 20A.

Although the examples illustrated in FIGS. 2A-2C include grooves 48A and 48B, in other examples, tool 20A may include fewer grooves 48 (e.g., only one groove 48) or more grooves 48 (e.g., three, four, or five grooves 48) configured to receive actuators 34. FIG. 3 is a schematic diagram illustrating exemplary tool 20B. The components of tool 20B are substantially similar to the components of tool 20A (FIG. 2A), except that tool 20B includes only one actuator 34A for moving tubing 24 in a proximal or distal direction. In the example illustrated in FIG. 3, body 30 of anchor deployment member 28 may define only one pathway or groove 48 extending between proximal end 44 and distal end 46 of body 30, corresponding to the single actuator 34A coupled to tubing 24. Actuator 34A of tool 20B shown in FIG. 3 may function in a manner similar to actuators 34 of tool 20A shown in FIG. 2A.

Actuators 34 (of both tools 20A and 20B) may have any configuration suitable for causing movement of tubing 24 in a proximal or distal direction within body 30 of anchor deployment member 28. For example, in some examples, instead of facilitating fluid motion of tubing 24 in both proximal and distal directions, actuators 34 may actuate a ratcheting mechanism such that allows motion in only one direction, e.g., a proximal direction, while preventing motion in the other direction, e.g., a distal direction. In some examples, actuators 34 that include a ratcheting mechanism may prevent movement of tubing 24 past a target tissue site within patient 10 once the target tissue site has been reached by tubing 24 and an IMD element has been positioned at the target tissue site.

FIG. 4 is a schematic diagram illustrating an exploded view of tool 20A (FIG. 2A) and an implantable medical device (IMD) element 50 that may be introduced into and anchored within patient 10 at a target tissue site using tool 20A. As shown in FIG. 4 and described above, tool 20A includes anchor 22, tubing 24 coupled to actuators 34A and 34B, needle 26, and anchor deployment member 28.

In the example illustrated in FIG. 4, IMD element 50 is an elongated member in the form of a lead configured to deliver electrical stimulation to a target tissue site of patient 10 via electrodes 52. However, although FIG. 4 illustrates IMD element 50 configured to deliver electrical stimulation, in other examples, IMD element 50 may be configured to deliver other types of therapy. For example, in some examples, IMD element 50 may be a catheter configured to deliver a fluid, e.g., a drug, to patient 10 to treat a disorder of patient 10.

Figure 4B:
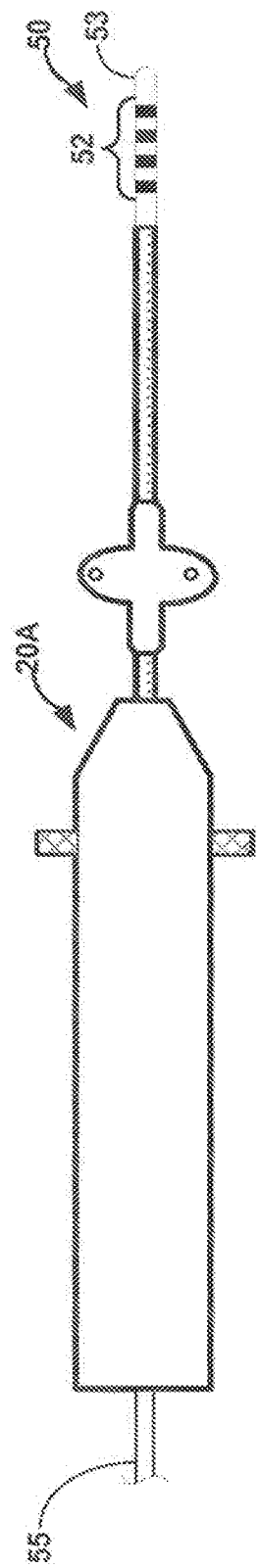
FIG. 4B is a schematic diagram of the assembled tool illustrated in FIG. 4A with the IMD element extending therethrough.

FIG. 4B illustrates the components of tool 20A in an assembled configuration, with implantable medical device element 50 extending through tool 20A. In the example illustrated in FIG. 4B, distal end 53 of IMD element 50, including electrodes 52, extends out of the distal end of tubing 24 and proximal portion 55 of IMD element 50 extends out of the proximal end of tubing 24 and anchor deployment member 28. In examples in which IMD element 50 is an electrical stimulation lead (e.g., the example illustrated in FIG. 4B), IMD element 50 may include one or more conductors extending within IMD element 50 electrically coupling electrodes 52 to one or more electrical contacts on a proximal end of the IMD element 50. The one or more electrical contacts may be configured to be coupled to an electrical stimulation generator such that IMD element 50 may deliver electrical stimulation therapy to patient 10.

Similarly, in examples in which IMD element 50 is a catheter configured to deliver drug therapy to patient 10, IMD element 50 may include one or more outlet ports on its distal end configured to dispense fluid to tissue of patient 10. The one or more outlet ports on the distal end may be in fluid communication with one or more inlet ports on a proximal end of IMD element 50, which are configured to be coupled to a fluid delivery pump such that IMD element 50 may deliver drug therapy to patient 10.

Figure 5A:
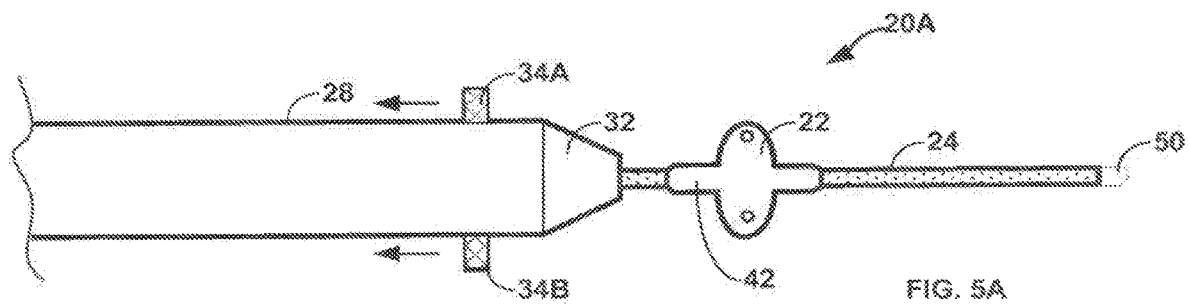
FIGS. 5A-5C are schematic diagrams illustrating various stages of deploying an anchor around an IMD element using the tool of FIGS. 2A-2C.
Figure 5B:
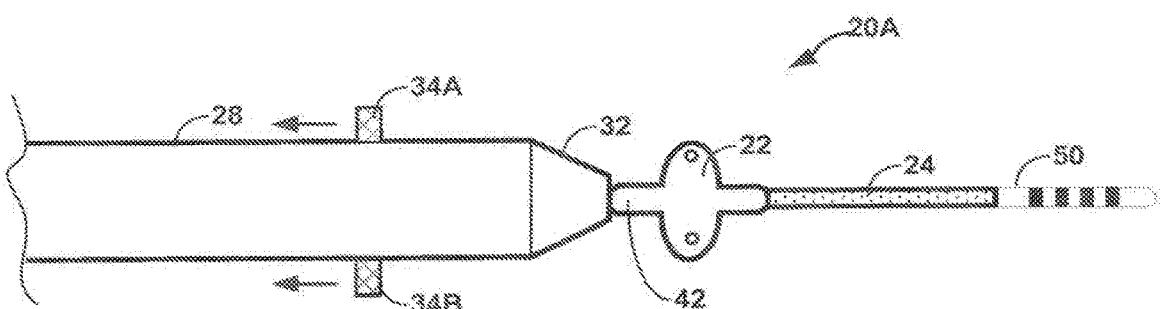
Figure 5C:
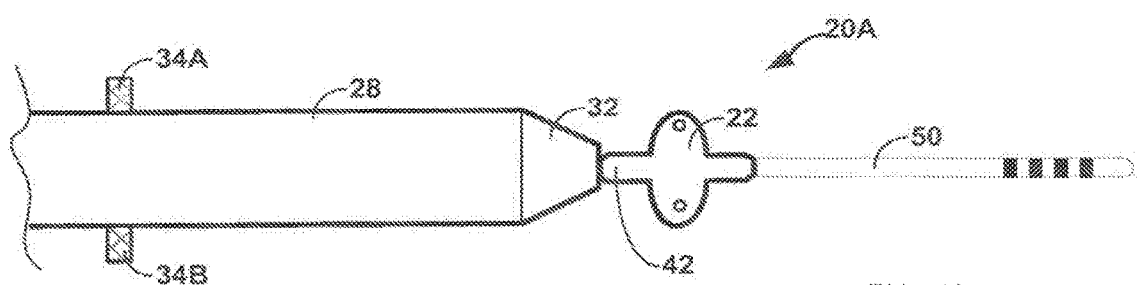

FIGS. 5A-5C are schematic diagrams illustrating tool 20A in various stages of deployment of anchor 22. As illustrated by the arrows in FIGS. 5A and 5B, actuators 34 (and consequently tubing 24) may be pulled in a proximal direction within body 30 of anchor deployment member 28 until anchor engagement element 32 abuts anchor 22 and forces anchor 22 onto IMD element 50 to deploy anchor 22.

As illustrated in FIG. 5A, anchor 22 is disposed around tubing 24, which is disposed around IMD element 50. A clinician or other user may apply a force to actuators 34 to pull actuators 34 in a proximal direction (as illustrated by the arrows in FIGS. 5A and 5B), which may cause tubing 24, coupled to actuators 34, and anchor 22, disposed around tubing 24, to move in a proximal direction while body 30 of anchor deployment member 28 remains substantially in place. As shown in FIG. 5B, anchor deployment member 28 and anchor 22 move toward one another (as a result of pulling of actuators 34 and tubing 24 in a proximal direction) until anchor engagement element 32 of anchor deployment member 28 abuts the proximal end of body 42 of anchor 22. As illustrated in FIG. 5C, the clinician or other user may continue to pull actuators 34 (and tubing 24) in a proximal direction while anchor engagement element 32 abuts anchor 22, causing tubing 24 to be retracted into anchor deployment member 28 and anchor 22 to be forced from tubing 24 onto the body of IMD element 50.

FIG. 6 illustrates exemplary tool 20C configured for introducing and anchoring IMD element 50 proximate to a target tissue site of patient 10. Tool 20C is substantially similar to tool 20A described above, except that tool 20C additionally includes distance markings 54 on an outer surface of body 30 of anchor deployment member 28. Distance markings 54 may function as an indication of how much of tubing 24 has moved relative to IMD element 50 as a result of a clinician or other user applying a force to actuators 34. For example, during introduction of IMD element 50 into tissue of patient 10, IMD element 50 may not be visible to the clinician or user implanting IMD element 50. Thus, distance markings 54 may provide a visual indicator of how far tubing 24 has been pulled back relative to IMD element 50, e.g., how many electrodes 52 of IMD element 50 are exposed. In some examples, the amount of space between each of distance markers 54 may directly correspond to the amount of space between each of electrodes 52. Thus, upon moving actuators 34 between two adjacent distance markings, a clinician or user may recognize that an additional one of electrodes 52 has been exposed outside of tubing 24 within the tissue of patient 10. As another example, distance markers 54 may be useful in visually indicating when tubing 24 is sufficiently retracted within anchor deployment member 28 such that IMD element 50 is sufficiently exposed to receive anchor 22.

Although FIG. 6 illustrates seven distance markings 54, in other examples, any suitable number and configuration of distance markings 54 may be utilized.

FIGS. 7A-7D illustrate an alternative tool 20D, which includes a moveable anchor engagement element 56. As shown in the cross-section of FIG. 4D, moveable anchor engagement element 56 forms a fully enclosed portion of anchor deployment member 60 such that distal end 57 of anchor engagement element 56 that contacts anchor 22 is fully enclosed. In some examples, anchor engagement element 56 that includes a fully enclosed distal end 57 creates a tighter interface between distal end 57 and tubing 24 such that an anchor 22 defined by a smaller profile, e.g., anchor 22B illustrated in FIG. 8B) may be deployed by tool 20D. That is, in some examples, fully enclosed distal end 57 prevents anchor 22 from being pushed into anchor engagement element 56, e.g., into a groove defined within anchor engagement element 56, during deployment of anchor 22.

Figure 7D:
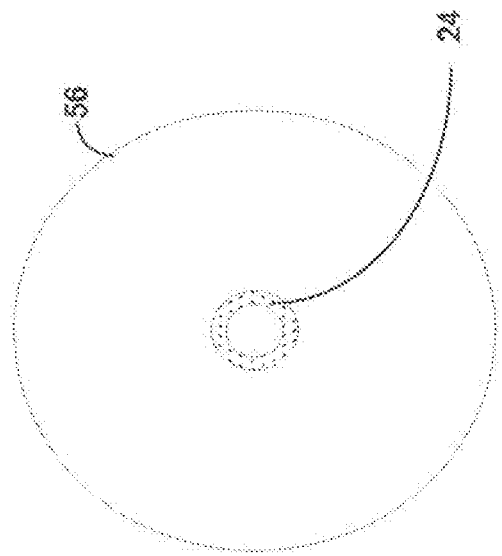

As illustrated in FIG. 7A, anchor engagement element 56 is separable from body 58 of anchor deployment member 60. Anchor engagement element 56 defines an aperture through which tubing 24 extends, as shown in the cross-section of FIG. 7D. Anchor engagement element 56 may slide proximally and distally along tubing 24 to engage or disengage with body 58 of anchor deployment member 60.

In some examples, a separable anchor engagement element 56 may be desirable to increase the ease of assembly of tool 20D, either in manufacturing or by an end user. For example, a user may thread the tubing 24 through the channel defined within anchor engagement element 56 and separately introduced into body 58 via groove 62, e.g., in a sideways manner.

In the example configuration illustrated in FIG. 7B, anchor engagement element 56 is engaged with or coupled to body 58. As illustrated, body 58 may define a groove 62 (shown in FIG. 7C) into which tubing 24 may be positioned such that tubing 24 extends through anchor deployment member 60. Groove 62 may be substantially similar to grooves 48 described with respect to FIGS. 2B and 2C. However, groove 62 extends only within body 58 and does not extend into anchor engagement element 56. Thus, distal end 57 of anchor engagement element 56 provides a substantially entirely enclosed tip that contacts anchor 22.

Figure 7C:
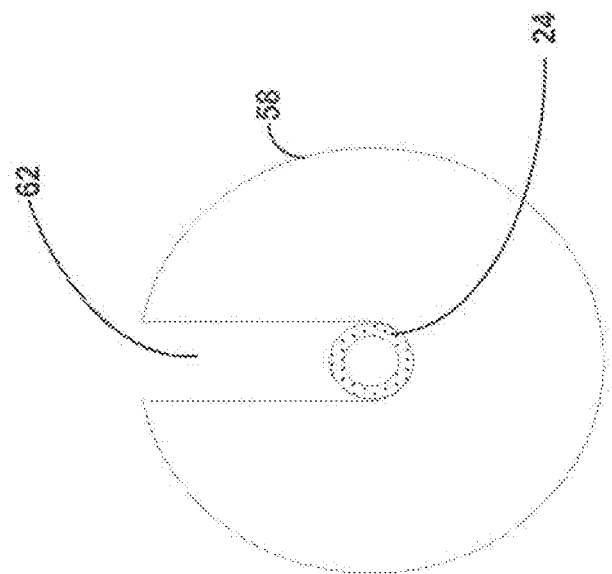

FIG. 7C illustrates a cross-section of tool 20D (FIGS. 7A and 7B) taken along the line 7C-7C shown in FIG. 7B. Thus, FIG. 7C illustrates a cross section of body 58 of anchor engagement element 60. As shown in FIG. 7C, body 58 may define a groove 62 into which tubing 24 can be positioned, e.g., to reduce the complexity of assembly of tool 20D (as described above with respect to FIGS. 2A-2C). FIG. 7D illustrates a cross-section of tool 20D taken along the line 7D-7D shown in FIG. 7B. As shown in FIG. 7D, anchor engagement element 56 substantially entirely encloses tubing 24.

Anchor engagement element 56 may be coupled to body 58 in any suitable manner. For example, in some examples, anchor engagement element 56 and body 58 may each include portions of a snapping mechanism configured to mate with one another to couple anchor engagement element 56 and body 58. In other examples, after tubing 24 has been inserted into both anchor engagement element 56 and body 58, anchor engagement element 56 and body 58 may be coupled using an adhesive.

FIGS. 8A-8D illustrate various exemplary configurations of anchors 22A-22D, respectively. It will be understood, however, that anchor 22 may have any configuration suitable for anchoring IMD element 50 within tissue of patient 10.

Figure 8A:
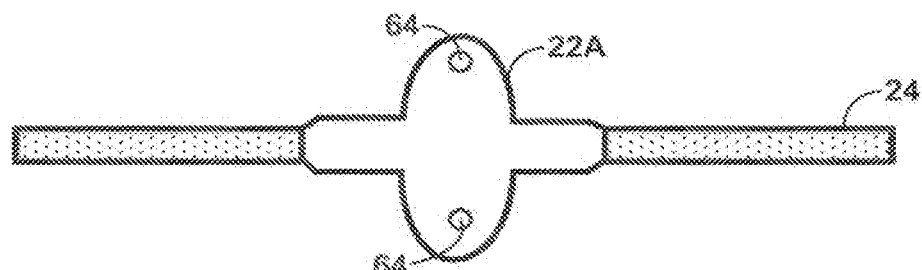
FIGS. 8A-8D are schematic diagrams illustrating several example configurations of an anchor that can be deployed around an implantable medical device using the tools described herein.
Figure 8B:
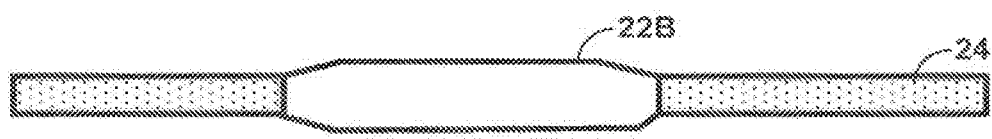
Figure 8C:
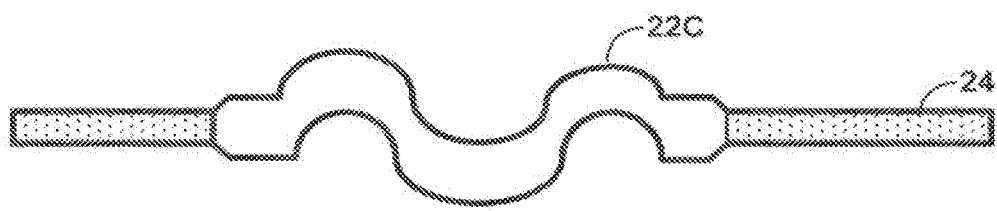
Figure 8D:
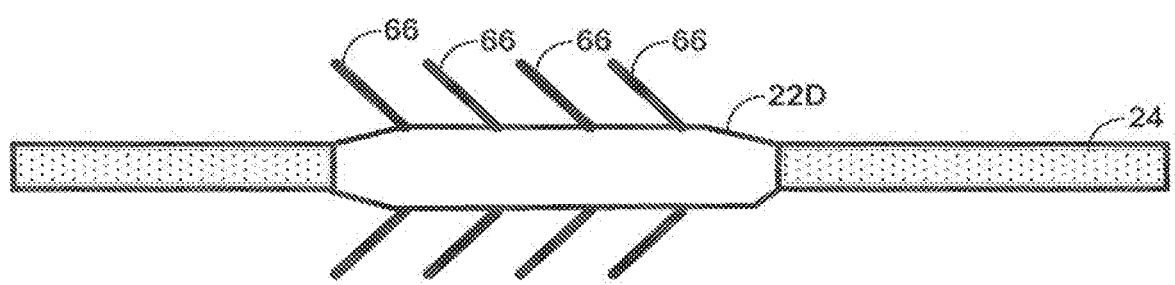

FIG. 8A illustrates anchor 22A which is configured to be sutured within patient 10 upon deployment. As illustrated, anchor 22A includes suture holes 64 configured to accept one or more sutures that can be threaded through suture holes 64 and through tissue of patient 10 to secure anchor 22A in place. FIG. 8B illustrates anchor 22B which may be a low-profile anchor. In some examples, a low-profile anchor 22B may reduce the amount of irritation of tissue of patient 10, in comparison to a more high-profile or bulky anchor. In some examples, the low-profile anchor 22B may also be configured to be sutured within tissue of patient 10. e.g., may include one or more suture holes. FIG. 8C illustrates anchor 22C which has a sinusoidal configuration that may reduce strain on anchor 22C and IMD element 50 positioned within anchor 22C (after deployment) and simultaneously secure anchor 22C within tissue of patient 10. In some examples, anchor 22C defined by a sinusoidal configuration may also include suture holes configured to be sutured within tissue of patient 10. FIG. 8D illustrates anchor 22D which includes tines 66 configured to retain anchor 22D and IMD element 50 within tissue of patient 10. Anchor 22D may include any suitable number of tines 66 arranged in any suitable configuration. In some examples, all of tines 66 may be oriented in the same direction, e.g., as shown in FIG. 8D, to prevent movement of anchor 22D in a particular direction. In other examples, some of tines 66 may be oriented in different directions to prevent movement of anchor 22D in various directions within tissue of patient 10. In each of the examples illustrated in FIGS. 8A-8D, at least a portion of anchor 22A-22D is elastic such that, upon retraction of tubing 24 into anchor deployment member 28, anchor 22A, 22B, 22C, or 22D bites down on the IMD element 50.

Figure 9:
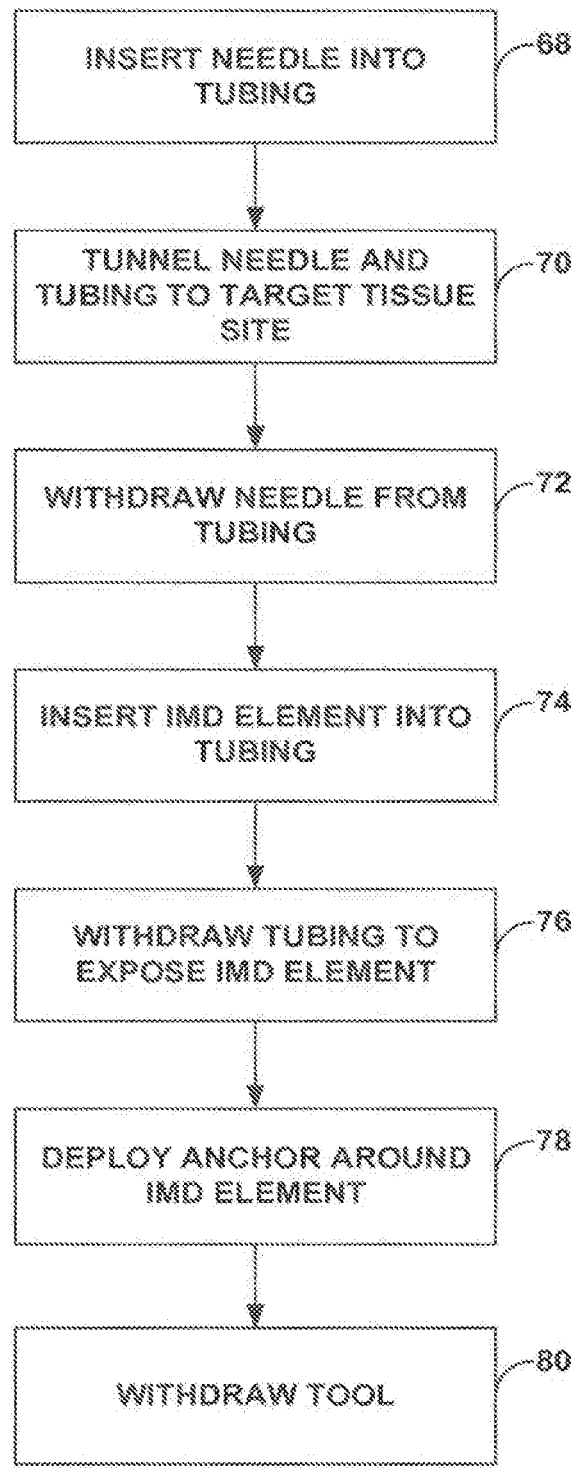
FIG. 9 is a flow diagram illustrating a technique for introducing and anchoring an IMD element within a patient.

FIG. 9 is a flow diagram illustrating a technique for introducing and anchoring IMD element 50 using the tools described herein. Although FIG. 9 is described using tool 20A (FIGS. 2A-2C), any of the tools described herein for introducing and anchoring an IMD element may be utilized with the technique.

According to the technique illustrated in FIG. 9, a clinician or other user may insert needle 26 into proximal end 31 of tubing 24 (68). As described above, tubing 24 may already be positioned within the channel defined within anchor deployment element 28, and the clinician may insert needle 26 into tubing 24 positioned within the channel. Tubing 24 is configured to slidably receive at least a portion of needle 26 via proximal end 31. The clinician or other user may subsequently tunnel needle 26 and tubing 24 to a target tissue site, such as a target nerve or muscle, within patient 10 (70). As described above, in some examples, needle 26 may be specifically configured to define a path through tissue of patient 10. For example, needle 26 may be configured with a sharp distal tip configured to puncture or push through tissue of patient 10.

Upon reaching the target tissue site, the clinician or other user may subsequently withdraw needle 26 from tubing 24 via proximal end 31 of tubing 24 (72). Tubing 24 may remain within the pathway defined by needle 26 through tissue of patient 10 in order to maintain the pathway for insertion of IMD element 50 into the pathway. After withdrawing needle 26 from tubing 24, the clinician or other user may subsequently insert IMD element 50 into tubing 24 via proximal end 31 of tubing 24 (74). Because tubing 24 was tunneled to the target tissue site within patient 10, the IMD element 50 inserted into tubing 24 will also be positioned at the target tissue site. After positioning IMD element 50 at the target tissue site, the clinician or other user may withdraw tubing 24 into body 30 of anchor deployment member 28 to expose the portion of IMD element 50 distal to anchor engagement element 32 (76). For example, as described above, the clinician or other user may apply a force to actuators 34 of tool 20A to pull tubing 24 (and anchor 22) proximally until anchor engagement element 32 abuts anchor 22. The clinician or other user may subsequently deploy anchor 22 around IMD element 50 to secure IMD element 50 within tissue of the patient (78). For example, with anchor engagement element 32 abutting anchor 22, the clinician or other user may subsequently continue to pull actuators 34 proximally such that anchor engagement element 32 forces anchor 22 off of tubing 24 and onto IMD element 50. In some examples, the clinician or other user may suture anchor 22 within tissue of the patient, e.g., in examples in which anchor 22 includes suture holes 64 (as illustrated in FIG. 8A). Upon deploying anchor 22 around IMD element 50, the clinician or other user may withdraw tool 20A from tissue of patient 10 (80). In some examples, therapy may subsequently be delivered to patient 10 via IMD element 50.

Various examples have been described. These and other examples are within the scope of the following claims.

What is claimed is:

1. An apparatus for introducing and anchoring an elongated implantable medical device element within a tissue of a patient, the apparatus comprising:

a first elongated member defining a proximal end and a distal end, the first elongated member configured to define a path through tissue of a patient for insertion of the implantable medical device element into the path;

a second elongated member defining a proximal opening, a distal opening, and a lumen extending between the proximal opening and the distal opening, the lumen configured to slidably receive at least a portion of the first elongated member and at least a portion of the implantable medical device element via the proximal opening, an anchor having an anchor lumen, the anchor being configured to secure the elongated implantable medical device in the path; and an anchor deployment member comprising:

a body defining a channel, wherein the first elongated member is slidable out of a proximal end of the channel, and an anchor engagement member configured to bear against the anchor when the second elongated member is moved in a proximal direction relative to the body such that the second elongated member is withdrawn from the anchor lumen.

2. The apparatus of claim 1, wherein the channel extends from a proximal end of the body to a distal end of the body, wherein the first elongated member, the second elongated member, and the implantable medical device element are slidable through the channel.

3. The apparatus of claim 1, wherein the first elongated member defines a first length, the channel defines a second length, and the first length is greater than the second length.

4. The apparatus of claim 1, wherein the anchor lumen is configured to slidably receive at least a portion of the second elongated member.

5. The apparatus of claim 4, wherein the anchor comprises at least one of a low-profile anchor, a sinusoidal configuration, or tines.

6. The apparatus of claim 1, wherein the first elongated member defines a lumen configured to slidably receive the elongated implantable medical device element.

7. The apparatus of claim 1, further comprising at least one actuator coupled to the second elongated member, wherein the at least one actuator is configured such that movement of the at least one actuator toward the proximal opening causes movement of the second elongated member toward the proximal opening.

8. The apparatus of claim 7, wherein the second elongated member is configured such that the movement of the second elongated member toward the proximal opening comprises movement of the second elongated member relative to the anchor.

9. The apparatus of claim 1, further comprising at least one distance marking on an outer surface of the body of the anchor deployment member, wherein the at least one distance marking is visually indicative of a position of the second elongated member relative to the anchor deployment member.

10. The apparatus of claim 1, wherein the anchor engagement member is separable from the body of the anchor deployment member, wherein the anchor engagement member is configured to substantially completely enclose the elongated implantable medical device element.

11. A method for introducing and anchoring an elongated implantable medical device element within a tissue of a patient, the method comprising:

defining a path through the tissue of the patient for insertion of the elongated implantable medical device element into the path, wherein defining the path through tissue of the patient comprises tunneling through tissue of the patient with a first elongated member of a medical device apparatus comprising:

the first elongated member defining a proximal end and a distal end, the first elongated member configured to define the path through the tissue of the patient for insertion of the implantable medical device element into the path;

a second elongated member defining a proximal opening, a distal opening, and a lumen extending between the proximal opening and the distal opening, the lumen configured to slidably receive at least a portion of the first elongated member and at least a portion of the implantable medical device element via the proximal opening, an anchor having an anchor lumen, the anchor being configured to secure the elongated implantable medical device in the path; and an anchor deployment member comprising:

a body defining a channel, wherein the first elongated member is slidable out of a proximal end of the channel, and an anchor engagement member configured to bear against the anchor when the second elongated member is moved in a proximal direction relative to the body such that the second elongated member is withdrawn from the anchor lumen.

12. The method of claim 11, wherein the channel extends from a proximal end of the body to a distal end of the body, wherein the first elongated member, the second elongated member, and the implantable medical device element are slidable through the channel.

13. The method of claim 11, wherein the first elongated member defines a first length, the channel defines a second length, and the first length is greater than the second length.

14. The method of claim 11, further comprising, prior to defining the path through tissue of the patient, inserting the first elongated member into the second elongated member, wherein defining the path through tissue of the patient comprises tunneling the first and second elongated members through tissue of the patient.

15. The method of claim 14, further comprising withdrawing the first elongated member from the second elongated member.

16. The method of claim 14, further comprising inserting the elongated implantable medical device element into the lumen of the second elongated member via the proximal opening of the second elongated member.

17. The method of claim 16, further comprising withdrawing the second elongated member to expose at least a portion of the elongated implantable medical device element.

18. The method of claim 17, further comprising deploying the anchor around the exposed portion of the elongated implantable medical device element, wherein the anchor lumen is configured to slidably receive at least a portion of the second elongated member and the elongated implantable medical device element.

19. The method of claim 18, wherein deploying the anchor around the exposed portion of the elongated implantable medical device element comprises moving the second elongated member in a proximal direction relative to the body of the anchor deployment member such that the second elongated member is withdrawn from the anchor lumen.

20. The method of claim 18, wherein deploying the anchor around the exposed portion of the elongated implantable medical device element comprises suturing the anchor to tissue of the patient.

21. The method of claim 18, further comprising withdrawing the second elongated member from tissue of the patient.

22. The method of claim 11, wherein tunneling through tissue of the patient with a first elongated member of a medical device apparatus comprises tunneling through tissue of the patient with the first elongated member of the medical device apparatus to a target tissue site within the patient.

23. A system for introducing and anchoring an implantable medical device element within a tissue of a patient, the system comprising:
  an implantable medical device element, wherein the implantable medical device element is configured to deliver therapy to a target tissue site within a patient; and
  an apparatus comprising:
    a first elongated member defining a proximal end and a distal end, the first elongated member configured to define a path through tissue of a patient for insertion of the implantable medical device element into the path;
    a second elongated member defining a proximal opening, a distal opening, and a lumen extending between the proximal opening and the distal opening, the lumen configured to slidably receive at least a portion of the first elongated member and at least a portion of the implantable medical device element via the proximal opening,
    an anchor having an anchor lumen, the anchor being configured to secure the elongated implantable medical device in the path; and
    an anchor deployment member comprising:
      a body defining a channel, wherein the first elongated member is slidable out of a proximal end of the channel, and
      an anchor engagement member configured to bear against the anchor when the second elongated member is moved in a proximal direction relative to the body such that the second elongated member is withdrawn from the anchor lumen.

24. The system of claim 23, wherein the anchor lumen is configured to slidably receive at least a portion of the second elongated member.

25. The system of claim 24, wherein the elongated implantable medical device element comprises at least one of a medical lead configured to deliver electrical stimulation therapy to the patient or a catheter configured to deliver drug therapy to the patient.

* * * * *